United States Patent [19]

Napp

[11] Patent Number: 4,528,139

[45] Date of Patent: Jul. 9, 1985

[54] PROCESS FOR OBTAINING ETHANOLIC PHOSPHATIDE FRACTIONS HIGHLY ENRICHED WITH PHOSPHATIDYLCHOLINE

[75] Inventor: Wolfgang Napp, Cologne, Fed. Rep. of Germany

[73] Assignee: A. Nattermann GmbH & Coe KG, Cologne, Fed. Rep. of Germany

[21] Appl. No.: 514,003

[22] Filed: Jul. 15, 1983

[30] Foreign Application Priority Data

Jul. 20, 1982 [DE] Fed. Rep. of Germany ....... 3227001

[51] Int. Cl.³ .......................... A23J 7/00; C07F 9/02; C07F 9/10; C11C 3/00
[52] U.S. Cl. ..................................................... 260/403
[58] Field of Search ........................................ 260/403

[56] References Cited

U.S. PATENT DOCUMENTS

| | | | |
|---|---|---|---|
| 2,724,649 | 11/1955 | Julian et al. | 260/403 |
| 2,727,046 | 12/1955 | Scholfield et al. | 260/403 |
| 2,945,869 | 7/1960 | Meyer et al. | 260/403 |
| 3,031,478 | 4/1962 | Klenk et al. | 260/403 |
| 3,544,605 | 12/1970 | Betzing et al. | 260/403 |
| 3,661,946 | 5/1972 | Pardun | 260/403 |
| 4,235,793 | 11/1980 | Betzing | 260/403 |
| 4,323,563 | 4/1982 | Takami et al. | 260/403 |

*Primary Examiner*—Helen M. S. Sneed
*Attorney, Agent, or Firm*—Pearne, Gordon, Sessions, McCoy, Granger & Tilberry

[57] ABSTRACT

The invention relates to a process for the preparation of phosphatide fractions highly enriched with phosphatidylcholine by warming up an ethanolic extract of de-oiled crude phosphatides at elevated temperatures before the addition of the aluminum oxide and continuing intensive stirring at elevated temperatures until the equilibrium saturation concentration is established.

8 Claims, No Drawings

PROCESS FOR OBTAINING ETHANOLIC PHOSPHATIDE FRACTIONS HIGHLY ENRICHED WITH PHOSPHATIDYLCHOLINE

The invention relates to a process for the preparation of phosphatide fractions highly enriched with phosphatidylcholine by intensive stirring of an ethanolic extract of de-oiled crude phosphatides in the presence of aluminum oxide at elevated temperatures.

Processes for the purification of phosphatide fractions by stirring chromatography on aluminum oxide are known per se.

Swiss Patent Specification No. 361,088 and U.S. Pat. No. 2,945,869 describe a purification process for obtaining soybeanphosphatide fractions which are to be used as emulsifiers for fat emulsions to be administered intravenously. In this process, alcoholic solutions of crude phosphatides which have already been de-oiled or have a greatly depleted oil content are treated with aluminium oxide at room temperature thereby to deplete the solutions of phosphatidylethanolamine and, in particular, to free them substantially from phosphatidylinositol.

German Patent Specification No. 2,718,797 (U.S. Pat. No. 4,235,793), Patent of Addition to German Patent Specification No. 1,617,680 and German Patent Specification No. 1,617,679 (U.S. Pat. No. 3,544,605) disclose a purification process in which ethanolic extracts of oil-containing crude phosphatides are used as the starting substances. In this process, the alcoholic extracts thus obtained are stirred intensively at room temperature in the presence of aluminum oxide for 2.5 to 4 hours.

Both processes have the common factor that the purification operations are carried out at room temperature.

It is an object of the present invention to provide for an improved process for purification allowing to obtain ethanolic phosphatide fractions more highly enriched with phosphatidylcholine and with less aluminum oxide adsorption agent in comparison to the above prior art processes.

In the process according to the invention, stirring chromatography of the ethanolic extracts with aluminum oxide is carried out at elevated temperatures, preferably at temperatures above 50° C., which leads to a surprisingly great reduction in the time necessary for saturation of the aluminum oxide. As comparative experiments have shown, the purification effect achieved after 60 minutes at 20° C. is already achieved within 5 minutes at the most preferred temperature of 60° C. Application of temperatures above 50° C. has not hitherto been regarded as feasible, since decomposition reactions were feared.

Surprisingly, however, no change in the product quality have been found even with prolonged contact times of 60 minutes at the most preferred temperature of 60° C. Moreover, the time required for saturation of the aluminum oxide is greatly shortened by increasing the operating temperature of the stirring chromatography to temperatures of 60° C. or more, which results in a drastically reduced aluminum oxide requirement, since only partial loading of the aluminum oxide is achieved at room temperature.

The alcohol extracts used as starting substances in the process according to the invention are prepared from de-oiled crude vegetable phosphatides, in particular crude soybean phosphatide, by extraction with 96% strength ethanol.

The extract solution, which can additionally be diluted, if necessary, with 96% strength ethanol, is heated to an elevated temperature, preferably above 50° C. before addition of the aluminum oxide, and kept at the desired temperature, preferably 60° C., until the equilibrium saturation concentration is established. The amount of aluminum oxide required is calculated from the amount of dissolved solid in the extract solution, taking into consideration the phosphatidylethanolamine content, and is 2.5 to 3.5 times the solids content. After the envisaged contact time between the extract solution and the aluminum oxide, the laden aluminum oxide is separated off immediately. The phosphatide fractions according to the invention which are obtained after evaporation of the solvent in vacuo have a phosphatidylcholine content of 70 to 75%.

The process according to the invention is illustrated in more detail by the following examples.

EXAMPLE 1

(a) 5 liters of an ethanolic phosphatide extract solution (of de-oiled crude soybean phosphatide) with a solids content of 6.37%, composed of 50.9% of phosphatidylcholine, 17.4% of phosphatidylethanolamine and 0.9% of lysophosphatidylcholine and having an acid number of 16.6 (all values based on the dry substance) were stirred intensively with 2 liters of 96% strength ethanol and 1.1 kg of $\gamma$-Al$_2$O$_3$ in a stirred container at 60° C. for 5 minutes. Before the experiment, the solution had already been heated to the experimental temperature. After the stirring time, the laden Al$_2$O$_3$ is immediately separated off from the solution. The clear solution is evaporated to dryness in vacuo.

Yield: 161 g of solid (phosphatide fraction)=yield of solid of 63% of theory.

The phosphatide fraction thus prepared was composed of: 75.4% of phosphatidylcholine, 6.6% of phosphatidylethanolamine and 1% of lysophosphatidylcholine and had an acid number of 5.64 (all values based on the dry substance).

(b) For comparison, a batch analogous to that in experimental section (a) was intensively stirred (also with 1.1 kg of $\gamma$-Al$_2$O$_3$), but at 20° C. for 60 minutes, and was worked up as described above.

Yield: 145 g of solid (phosphatide fraction)=yield of solid of 57% of theory.

The phosphatide fraction thus prepared was composed of: 75.4% of phosphatidylcholine, 4.2% of phosphatidylethanolamine and 1% of lysophosphatidylcholine and had an acid number of 2.26 (all values based on the dry substance).

EXAMPLE 2

(a) 5 liters of an ethanolic phosphatide extract solution (of de-oiled crude soybean phosphatide) with a solids content of 6.37%, composed of 50.9% of phosphatidylcholine, 17.4% of phosphatidylethanolamine and 0.9% of lysophosphatidylcholine and having an acid number of 16.6 (all values based on the dry substance) were diluted with 2 liters of 96% strength ethanol, heated to 60° C. and stirred intensively together with 0.79 kg of $\gamma$-Al$_2$O$_3$ in a stirred container at 60° C. for 40 minutes. After the stirring time, the laden Al$_2$O$_3$ was immediately separated off from the solution. The clear solution was evaporated to dryness in vacuo.

Yield: 188 g of solid (phosphatide fraction) = yield of solid of 74% of theory.

The phosphatide fraction thus prepared was composed of: 69.8% of phosphatidylcholine, 5.4% of phosphatidylethanolamine and 1% of lysophosphatidylcholine. (b) For comparison, 5 liters of ethanolic extract solution of the same composition as described under (a) were diluted with 2 liters of 96% strength ethanol and stirred intensively with 1.0 kg of $\gamma$-$Al_2O_3$ at 20° C. for 40 minutes. The laden $Al_2O_3$ was then immediately separated off from the solution.

The clear solution was evaporated to dryness in vacuo.

Yield: 178 g of solid (phosphatide fraction) = yield of solid of 70% of theory.

The phosphatide fraction thus prepared for comparison was composed of: 69.9% of phosphatidylcholine, 5.7% of phosphatidylethanolamine and 1.1% of lysophosphatidylcholine (all values based on the dry substance).

The phosphatide fractions thus prepared are always free from monophosphatidylinositol.

What I claim is:

1. Process for the preparation of phosphatide fractions highly enriched with phosphatidylcholine by treatment of a solution of an ethanol extract obtained from commercially available de-oiled crude vegetable phosphatides with aluminum oxide, comprising warming up the ethanol solution to an elevated temperature before the addition of the aluminum oxide, mixing this warmed up ethanol solution with 2.5 to 3.5 times the amount, based on the solids content, of aluminum oxide, stirring the mixed ethanol solution and aluminum oxide at temperatures between 50° C. and 70° C. until the equilibrium saturation concentration is established, separating the laden aluminum oxide, and evaporating to dryness the resulting clear solution to provide the phosphatide fractions.

2. Process as claimed in claim 1 wherein the ethanol solution, before the addition of the aluminum oxide, is warmed to an elevated temperature above 50° C.

3. Process as claimed in claim 1 wherein stirring is performed at about 60° C.

4. Process as claimed in claim 1 wherein gamma-aluminum oxide is used as the aluminum oxide adsorption agent.

5. Process as claimed in claim 2 wherein stirring is performed at about 60° C.

6. Process as claimed in claim 2 wherein gamma-aluminum oxide is used as the aluminum oxide adsorption agent.

7. Process as claimed in claim 3 wherein gamma-aluminum oxide is used as the aluminum oxide adsorption agent.

8. Process as claimed in claim 5 wherein gamma-aluminum oxide is used as the aluminum oxide adsorption agent.

* * * * *